(12) United States Patent
Mather

(10) Patent No.: US 8,584,837 B1
(45) Date of Patent: Nov. 19, 2013

(54) RAZOR BLADE STORAGE AND STERILIZATION DEVICE

(71) Applicant: Wayne C. Mather, Whistler (CA)

(72) Inventor: Wayne C. Mather, Whistler (CA)

( * ) Notice: Subject to any disclaimer, the term of this patent is extended or adjusted under 35 U.S.C. 154(b) by 0 days.

(21) Appl. No.: 13/723,522

(22) Filed: Dec. 21, 2012

(51) Int. Cl.
B65D 81/22 (2006.01)

(52) U.S. Cl.
USPC .......................................... 206/208; 134/157

(58) Field of Classification Search
USPC ................. 206/205, 207, 208, 352, 354, 359; 134/157; 15/104.93
See application file for complete search history.

(56) References Cited

U.S. PATENT DOCUMENTS

| | | | |
|---|---|---|---|
| 2,465,440 A * | 3/1949 | Fleckenstine | 15/218 |
| 3,019,494 A * | 2/1962 | Horie et al. | 206/208 |
| 3,759,594 A | 9/1973 | Cobb | |
| 5,007,533 A | 4/1991 | Purohit | |
| 5,251,752 A | 10/1993 | Purohit | |
| 5,958,394 A | 9/1999 | Smith | |
| 6,145,657 A | 11/2000 | Cox | |
| 6,634,492 B1 | 10/2003 | Cox | |
| 7,858,027 B2 * | 12/2010 | Trissel | 422/7 |
| 2003/0101525 A1 | 6/2003 | Belloli | |
| 2011/0225834 A1 * | 9/2011 | Cirilli | 30/541 |

* cited by examiner

Primary Examiner — Jacob K Ackun
(74) Attorney, Agent, or Firm — Montgomery Patent & Design; Robert C Montgomery

(57) ABSTRACT

A device for storing shaving razor blades in a manner which prolongs usability includes containment for storing cleaned razor blades and for storing a razor handle. The interior of the housing compartment comprises a reservoir configured for retaining a volume of a cleaning and preserving solution. After shaving, a user detaches the razor blade from the handle and places it within a blade cleaning assembly which provides a means to submerge the blade into the solution. The razor blade is then retrieved for subsequent shaving. The device also provides a removable blade cartridge being especially useful for storing clean blades while traveling.

15 Claims, 7 Drawing Sheets

RAZOR BLADE STORAGE AND STERILIZATION DEVICE

RELATED APPLICATIONS

The present invention was first described in U.S. Provisional Patent Application No. 61/578,406 filed on Dec. 21, 2011, the contents of which are incorporated herein by reference.

FIELD OF THE INVENTION

The present invention relates generally to a storage unit for a razor blade and, more particularly, to a storage and sterilization system for a razor blade handle and a plurality of disposable razor blades.

BACKGROUND OF THE INVENTION

There are many different methods of shaving available to the consumer today. Various electrical shavers, depilatory creams and lotions, wax treatments, and the like are available for both men and women. But perhaps the most common method of shaving used is still the razor blade. Most shavers today use a common shaving handle which accepts disposable blade mechanisms. After the blades become dull, the user simply replaces them in order to obtain a close shave. However, such replacement blades are very expensive and are likely to be only slightly cheaper than a new razor blade and handle system. Accordingly, there exists a need for a means by which razor blades as used as part of a shaving system can be provided with increased usable life in order to reduce periodic replacement costs.

One (1) of the primary downsides of this method is that such replacement blades are very expensive and are likely to be only slightly cheaper than a new razor blade and handle system. As such, the vast percentage of money spent on these razors is due to the razors. However, the razor blades are difficult to maintain due to the fact that they are in contact with various chemicals and with the user's face and are often stored while wet, factors contributing to degradation, rusting, dulling, and dirtying of the blades. As a result, razors are discarded more frequently than they would be if not exposed to the factors described above.

Having recognized the abovementioned problems, the inventor observed there remains a need for a means by which razor blades as used as part of a shaving system can be provided with increased usable life in order to reduce periodic replacement costs.

Several attempts have been made in the past to provide such an hygienic storage system for razors. U.S. Pat. No. 3,759,594, in the name of Cobb, discloses a container that receives and supports a razor so the cutting implement is in close proximity to a corrosion inhibitor, essentially a wicking material impregnated with an agent. Unfortunately, the Cobb invention is not under the overall scope of the present invention in that it does not provide a storage means for individual blades that can be removed for transport.

U.S. Pat. No. 5,007,533, issued in the name of Purohit, describes a wet blade storage apparatus comprising a razor holder supporting a razor and blade within a vessel of mineral oil. The present invention also comprises a removable container for the razors and blades and a portable carrying case for individual blades.

U.S. Pat. No. 6,145,657, issued in the name of Cox, discloses a housing attachable to a blade portion of a razor filled with a mineral oil and biocide solution. Unfortunately, the Cox device only attaches to n individual razor and does not provide a means to store and clean multiple razors and their blades as well as it does not provide a portable carrying case for individual blades.

U.S. Pat. No. 6,634,492, issued in the name of Cox, discloses a housing filled with a mineral oil and biocide solution and a stand to enable the upright position of a razor so that its blade is submerged in the solution. Unfortunately, the Cox device only attaches to n individual razor and does not provide a means to store and clean multiple razors and their blades as well as it does not provide a portable carrying case for individual blades.

None of the prior art particularly describes a storage system for cleaning and transporting razor blades and razors.

SUMMARY OF THE INVENTION

In view of the foregoing disadvantages inherent in the prior art, it has been observed that there is need of a means provide a system to enable cleaning and storage of razor blades.

An object of the present invention is to provide a container comprising an upper panel, a lower panel, a front panel, a rear panel, a first side panel, and a second side panel. A reservoir is inserted into the container through the upper panel and nests within a reservoir recess in the bottom panel. A blade storage means is inserted into a blade storage recess located on the first side panel. A blade cleaning assembly is hingedly attached to the front panel for inserting blades into the reservoir within the container.

A further object of the present invention is to provide a plurality of foot portions located on bottom ends of the corner portions of the container.

Another object of the present invention is to provide a lid to removably cover the reservoir aperture. The lid further has a gripping recess to aid in removal.

An object of the present invention is to provide a container a lid removably attached to a top of said container to removably cover said reservoir aperture;

Yet another object of the present invention is to provide a razor storage compartment located on the second side panel, further having an upper semi-circular compartment opening.

Yet another object of the present invention is to provide such a blade cleaning assembly further comprises having a door hingedly attached to the front panel, a latch, and an arcuate appendage extending inward from an inner side of said door and having a plurality of removably attached blade compartments.

Yet another object of the present invention is to provide such a reservoir having an open-top cylindrical vessel with a reservoir floor, an integral reservoir handle located along an upper rear surface of a first side. In another embodiment, the reservoir further has s a key feature disposed therewithin to correspondingly mate with a receiver of said reservoir recess in order to position said second side of said reservoir towards said front panel.

In an embodiment of the present invention, the blade storage means is a blade rack, comprising a five-sided rectangular enclosure and having a pair of integral clip portions located along opposing outer surfaces thereof to correspondingly mate with locking features adjacent to the blade storage recess. The blade rack further has at least one (1) lateral divider within said enclosure to define adjacent blade storage compartments, each further having a drain feature.

In another embodiment of the present invention, the blade storage means is a travel cartridge comprising a lower enclosure half having a proximal side and on opposing outer sidewalls thereof, an upper enclosure half having a proximal side, a rectangular gasket disposed between the proximal sides of enclosure halves. A pair of fasteners each removably attaches the enclosure halves together through aligned first aperture feature and second aperture feature pairs. A non-porous pad is adhesively affixed to an inner surface of said upper enclosure half. At least one (1) lateral divider is located within the lower enclosure half to define adjacent blade storage compartments, each further having a drain feature. a pair of integral clip portions located along opposing outer sidewalls of said lower enclosure half to correspondingly mate with locking features adjacent to the blade storage recess. Each blade storage compartment is configured to receive and retain a razor blade and the travel cartridge is adapted to receive a cleaning solution.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

| | |
|---|---|
| 10 | razor blade storage and sterilization device |
| 15 | corner feature |
| 20 | container |
| 22 | front panel |
| 24 | first side panel |
| 26 | rear panel |
| 28 | second side panel |
| 29 | foot |
| 30 | front opening |
| 32 | blade storage recess |
| 34 | upper panel |
| 35a | bottom panel |
| 35b | key feature |
| 36 | reservoir aperture |
| 37 | reservoir recess |
| 38 | reservoir |
| 39 | reservoir handle |
| 40 | lid |
| 41 | reservoir floor |

-continued

| | |
|---|---|
| 42 | cylinder |
| 43 | key recess |
| 44 | male thread |
| 45 | gripping recess |
| 46 | female thread |
| 50 | blade cleaning assembly |
| 52 | door |
| 54 | hinge |
| 56 | appendage |
| 57a | slot |
| 57b | tab |
| 58 | blade compartment |
| 59 | magnet |
| 60 | latch handle |
| 62 | latch |
| 64 | divider |
| 66 | drain feature |
| 80 | travel cartridge |
| 81a | first clip |
| 81b | second clip |
| 82 | lower enclosure half |
| 84 | upper enclosure half |
| 85a | male locking feature |
| 85b | female locking feature |
| 86 | knob fastener |
| 88a | upper fastener aperture |
| 88b | lower fastener aperture |
| 90 | gasket |
| 92 | rubber pad |
| 96 | razor storage compartment |
| 97 | compartment opening |
| 100 | solution |
| 105 | razor handle |
| 110 | blade |
| 150 | blade rack |

DETAILED DESCRIPTION OF THE PREFERRED EMBODIMENT

The best mode for carrying out the invention is presented in terms of its preferred embodiment, herein depicted within FIGS. 1 through 6b. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a razor blade storage and sterilization device (herein described as the "device") 10, which provides a means for cleaning, disinfecting, and increasing the longevity of disposable razor blades 110.

Figure 1:
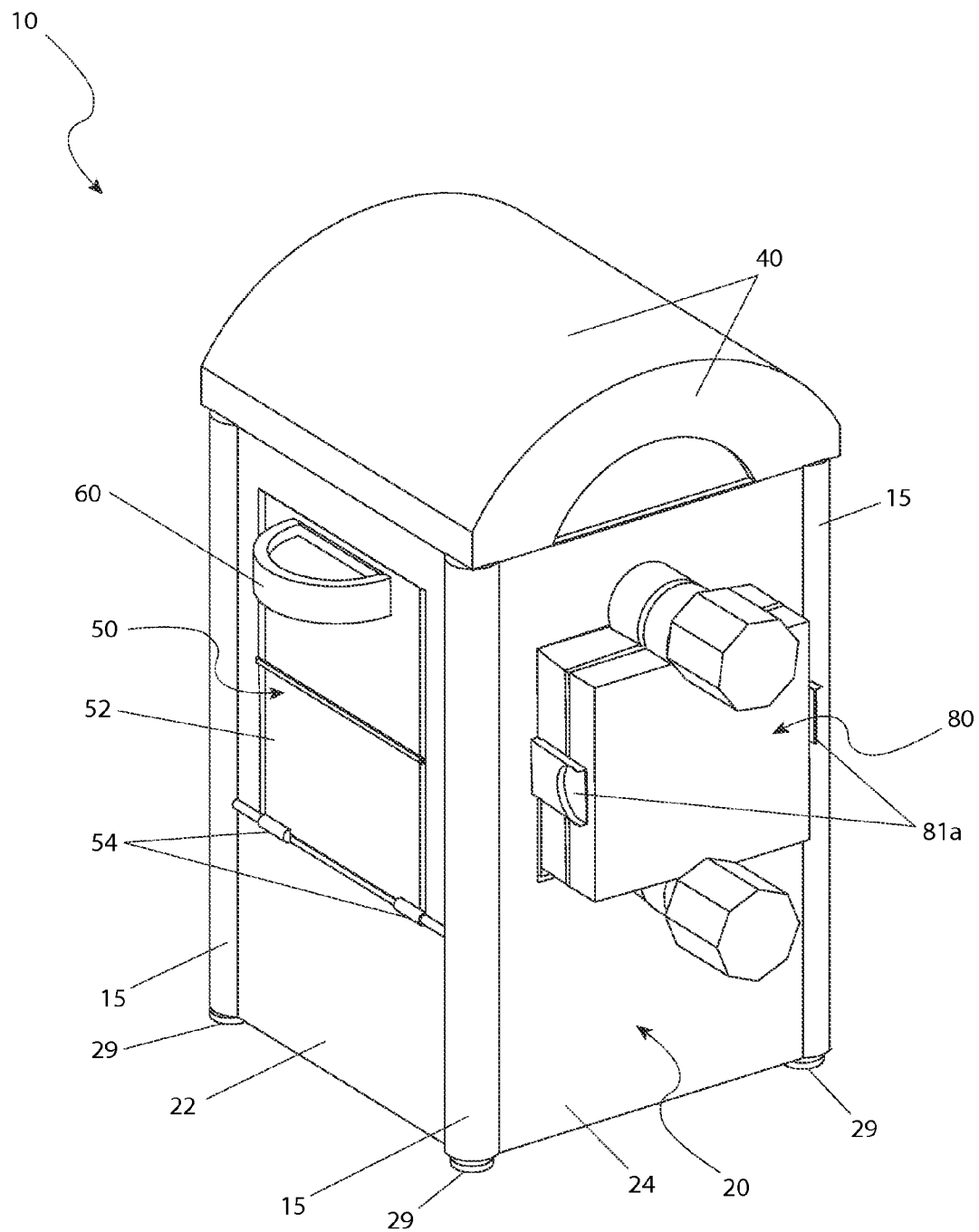
FIG. 1 is a front perspective view of a razor blade storage and sterilization device 10, according to a preferred embodiment of the present invention.
Figure 2:
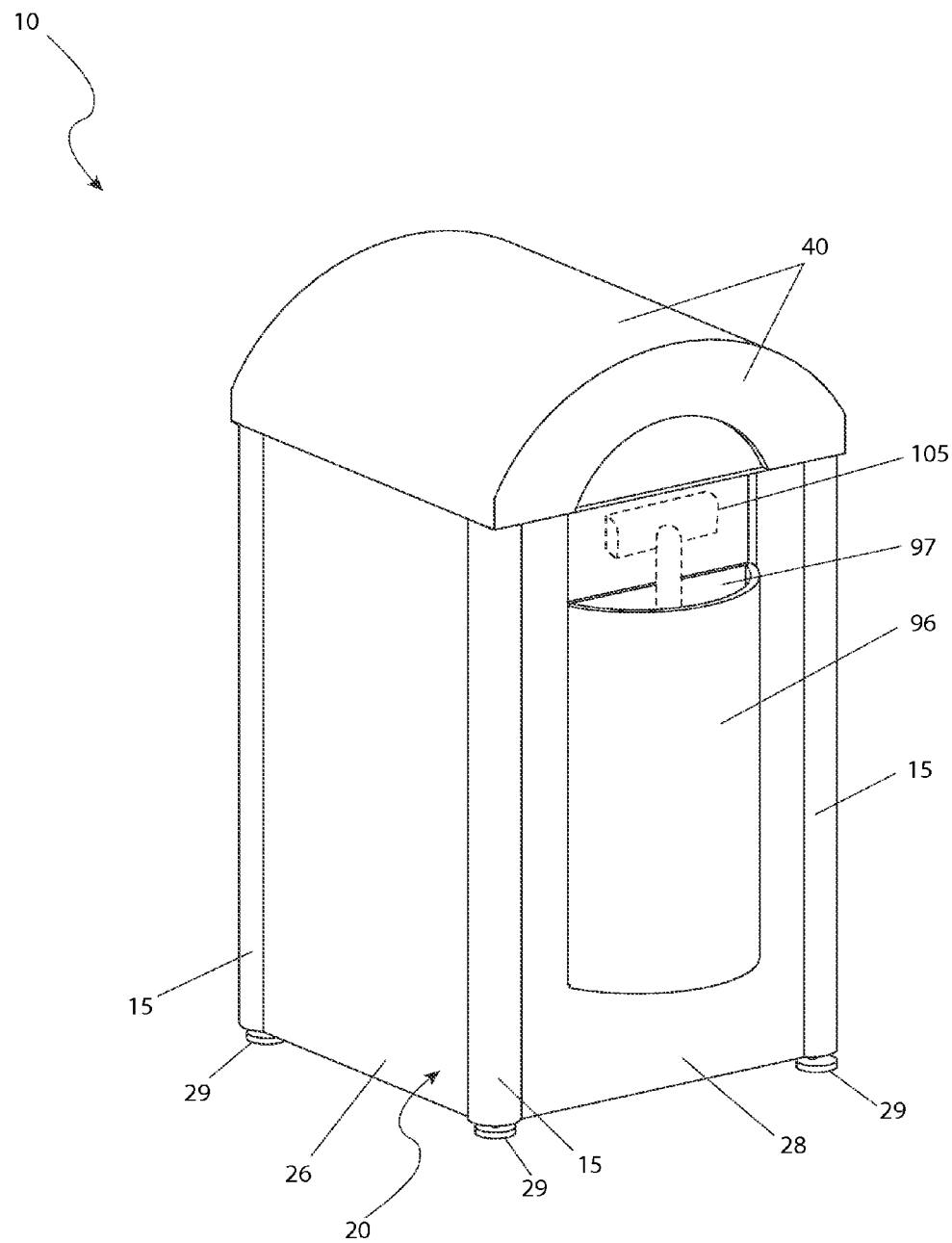
FIG. 2 is a rear perspective view of the razor blade storage and sterilization device 10, according to a preferred embodiment of the present invention.

Referring now to FIGS. 1 and 2, front and rear perspective views of the device 10 according to the preferred embodiment of the present invention are disclosed. The device 10 provides storage and disinfecting of disposable razor blades 110 within a container portion 20 which comprises a hollow unitary rectangular structure having six (6) sides including a front panel 22, a first side panel 24, a rear panel 26, a second side panel 28, an upper panel 34, and a bottom panel 35a. The panels 22, 24, 26, 28, 34, 35a are joined at vertical corner portions by decorative and rounded integral corner features 15.

The device 10 also comprises a half-cylinder-shaped razor storage compartment 96 being integrally-molded upon the second side panel 28, and having an upper semi-circular compartment opening 97 which allows a user to insert a razor handle 105 in a "ready" position, until needed for use.

Figures 4A, 4B:
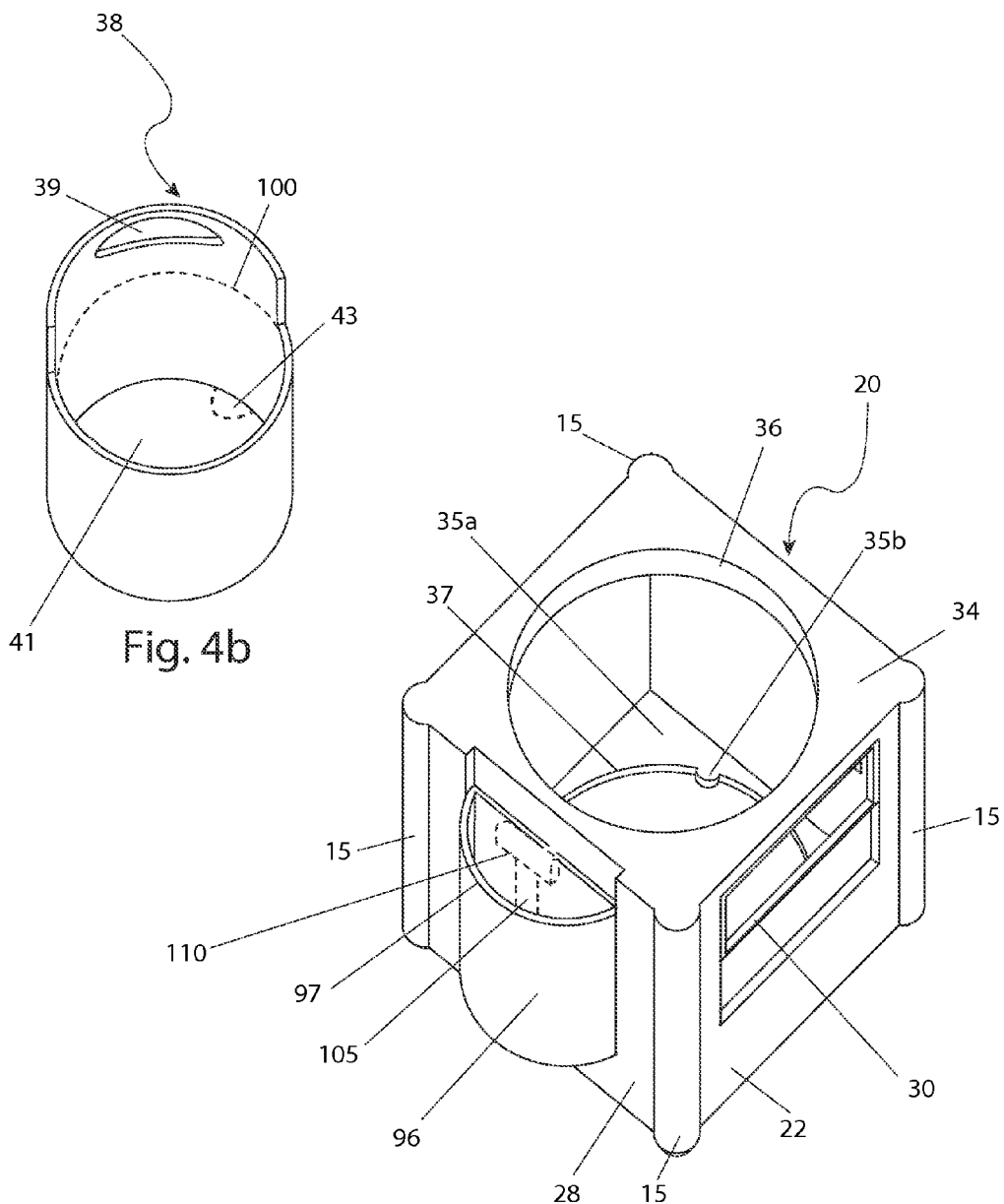
FIG. 4a is a top perspective view of the razor blade storage and sterilization device 10, according to a preferred embodiment of the present invention.
FIG. 4b is a top perspective view of a reservoir portion 38 of the razor blade storage and sterilization device 10, according to a preferred embodiment of the present invention.
Figure 5:
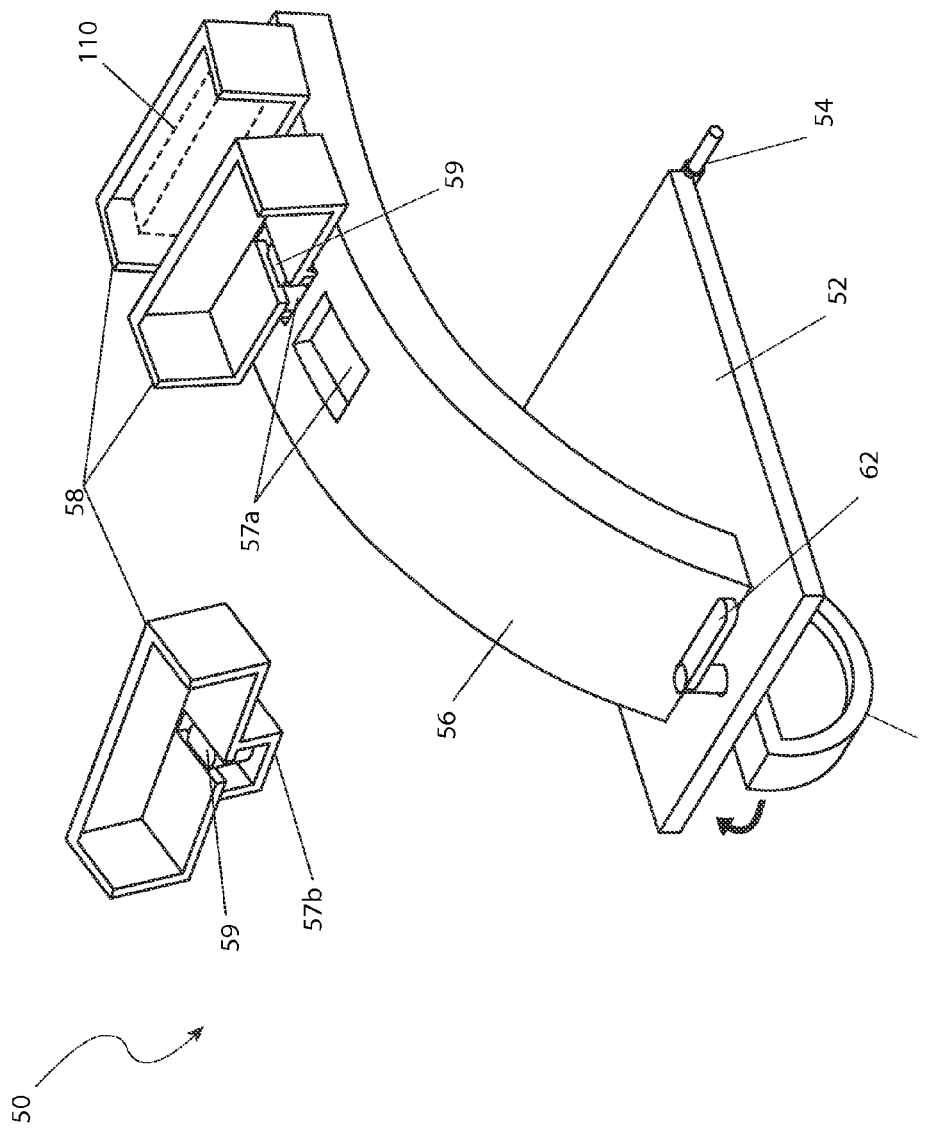
FIG. 5 is a close-up view of a door assembly portion 50 of the razor blade storage and sterilization device 10, according to a preferred embodiment of the present invention.

The front panel portion 22 of the container 20 comprises a pivoting blade cleaning assembly 50 which provides a means to position and submerse a plurality of blades 110 into cleaning solution 100 being contained within a reservoir 38 located within the container 20, thereby removing dirt, hair, bacteria, and other contaminants (see FIGS. 4 and 5).

The first side panel 24 further comprises a means to removable attach a travel cartridge 80 or a blade rack 150 via insertion into a molded-in blade storage recess 32. The blade storage recess 32 comprises a rectangular recess having a pair of square female locking features 85b being sized and positioned so as to engage corresponding male locking features 85a of the travel cartridge 80 and blade rack 150 portions. The travel cartridge 80 and blade rack 150 portions provide a means to store and/or transport a plurality of blades 110 (see FIGS. 3, 6a, and 6b).

The device 10 is preferably fabricated using durable plastic materials molded in various decorative colors; however, other equivalent materials may be utilized without limiting the scope of the device 10.

Figure 3:
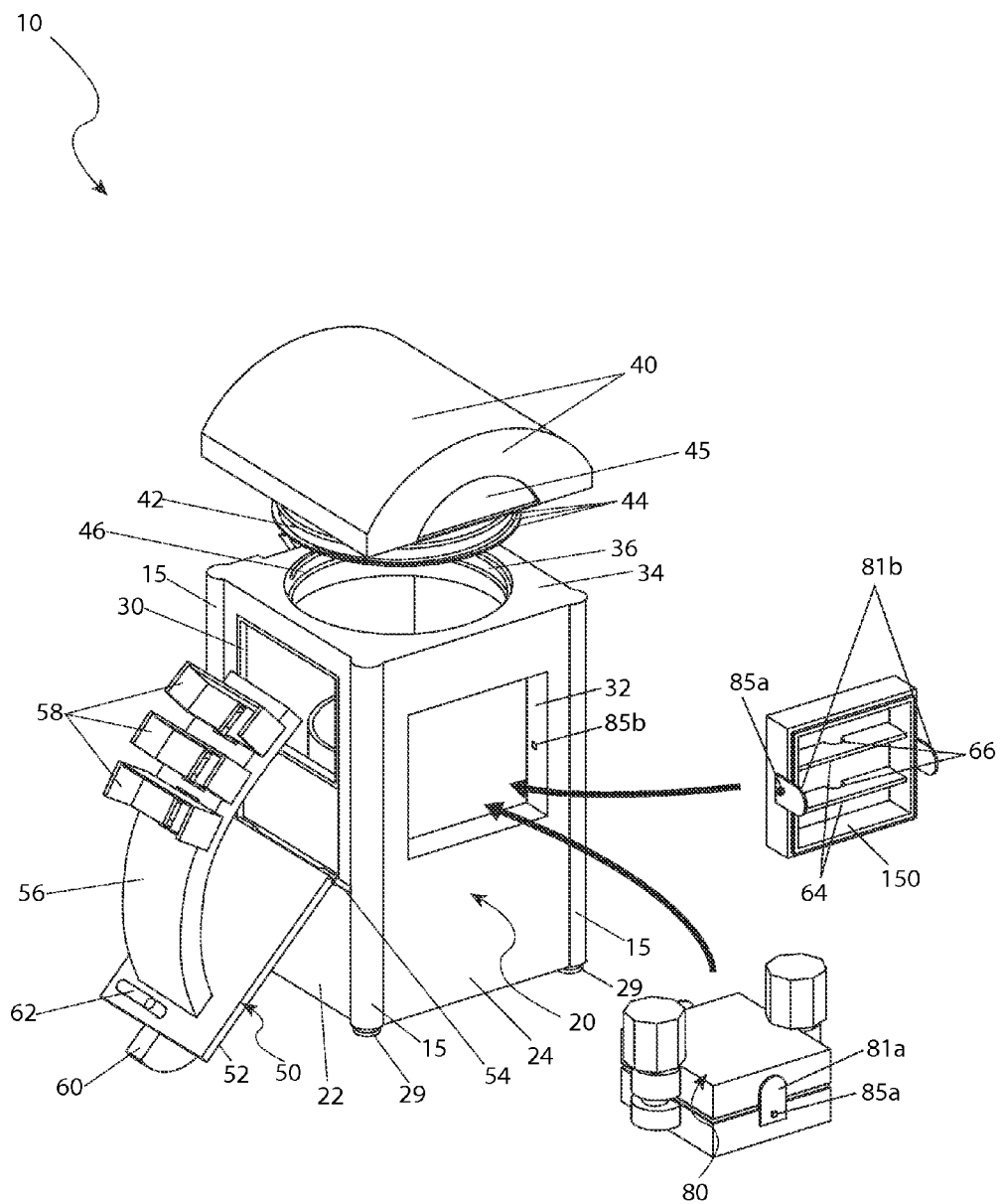
FIG. 3 is an exploded view of the razor blade storage and sterilization device 10, according to a preferred embodiment of the present invention.

Referring now to FIG. 3, an exploded view of the device 10, according to the preferred embodiment of the present invention, is disclosed. The container 20 comprises four (4) foot portions 29 being integrated into a bottom portion of each corner feature 15, located at each corner of the container 20. The feet 29 are preferably made of an anti-skid material such as rubber, thereby allowing the device 10 to be placed in a stable manner upon a flat level surface.

The upper panel portion 34 of the container 20 provides threaded attachment of a lid 40 via a circular reservoir aperture 36. The lid 40 further comprises an integral cylinder portion 42 which protrudes downwardly and engages the reservoir aperture 36. Said cylinder 42 and reservoir aperture 36 portions comprise respective male thread 44 and female thread 46 portions allowing the lid 40 to be threadingly retained and sealed upon the container 20, thereby minimizing evaporation of the contained solution 100 as well as shielding an internal portion of the container 20 from contaminates. The lid 40 preferably comprises an arcuate upper profile or other decorative grippable recess 45 on opposing sides to facilitate the gripping and removal of the lid 40.

The front panel 22 of the container 20 comprises a rectangular front opening 30 having a pair of hinges 54 along a bottom edge which provide pivoting attachment of a door portion 52 of the aforementioned blade cleaning assembly 50. The blade cleaning assembly 50 further comprises an appendage 56 having a plurality of removably attached blade compartments 58. The front opening 30 is particularly positioned so as to direct the arcuate appendage 56 containing from one (1) to three (3) blades 110 into a reservoir 38 within the container 20 as the door 52 pivots toward and covers the front opening 30. The blade compartments 58 are envisioned to be arranged in a parallel pattern forming a vertical column (also see FIG. 5). The door portion 52 of the blade cleaning assembly 50 comprises a rotary latch handle 60 and a corresponding internal latch portion 62 along a top edge which provides a quarter-turn mechanism to secure the blade cleaning assembly 50 in a closed state against the container 20.

The first side panel 24 of the container 20 includes the aforementioned blade storage recess 32 being recessed within said first side panel 24 and having female locking features 85b located along opposing vertical surfaces. Said blade storage recess 32 is sized to accept and affix the travel cartridge 80 or the blade rack 150 within. The travel cartridge 80 provides a sealed enclosure to store and sterilize a plurality of blades 110 in a portable manner. The travel cartridge 80 is to be secured within the blade storage recess portion 32 via a pair of integral second clips 81b (see FIGS. 6a and 6b).

The blade rack 150 comprises a five-sided rectangular enclosure having integral first clip portions 81a located along opposing outer vertical surfaces. Each first clip 81a further comprises a male locking features 85a. Said first clips 81a comprise outwardly extending flexible appendages which allow a user to squeeze the first clips 81a together to enable the male locking features 85a to engage the corresponding female locking features 85b within the blade storage recess 32, thereby retaining the blade rack 150 within the blade storage recess 32. The blade rack 150 further comprises two (2) equally-spaced lateral dividers 64 being molded-in features which allow insertion and retention of three (3) blades 110. The dividers 64 further comprise integral semi-circular drain features 66 to allow removal of residual solution 100.

As illustrated here, the components of the device 10 are designed for disassembly and cleaning when soiled.

Referring now to FIGS. 4a and 4b, perspective views of the container 20 and reservoir 38 portions of the device 10, according to a preferred embodiment of the present invention, are disclosed. The device 10 is shown here with lid 40 and blade cleaning assembly 50 portions removed for illustration sake. The device 10 includes a removable reservoir 38 which retains a volume of cleaning solution 100 envisioned to comprise a commercially-available cleaning and disinfecting product being capable of removing dirt, bacteria, and other contaminants from the submerged razor blades 110. The solution 100 is also envisioned to prevent rust and other forms of corrosion from forming on metal surfaces of the blades 110. The reservoir 38 comprises an open-top cylindrical vessel having a reservoir floor 41 and an integrally-molded ovular reservoir handle 39 which forms a grasping opening located along an upper rear surface allowing a user to grasp and lift the reservoir 38 out of the container 20. The container 20 provides a means to position and orient the reservoir 38 via a reservoir recess 37 and a key feature 35b formed into the bottom panel portion 35a. The reservoir recess 37 is correspondingly sized so as to slidingly receive a reservoir floor portion 41 of the reservoir 38 therein. The reservoir recess 37 further comprises a protruding semi-circular-shaped key feature 35b being positioned along a rear perimeter edge of said reservoir recess 37. During insertion and positioning of the reservoir 38, the key feature 35b interlocks with a mating key recess portion 43 molded into a bottom surface of the reservoir floor 41. The reservoir recess 37 and key feature 35b enable the reservoir 38 to engage the reservoir recess 37 in an orientated manner to assure proper alignment between the blade cleaning assembly 50 and the reservoir 38.

Referring now to FIG. 5 is a close-up view of the blade cleaning assembly portion 50 of the device 10, according to a preferred embodiment of the present invention, is disclosed. The blade cleaning assembly 50 is pivotingly attached to the front panel 22 via a pair of hinges 54 (see FIG. 3). The blade cleaning assembly 50 further comprises an assembly of portions including a flat rectangular door 52 and an arcuate appendage 56. The arcuate appendage 56 has a proximal end that extends perpendicularly from a rear surface of the door 52. The appendage 56 further comprises a plurality of blade compartments 58 being positioned in an equally-spaced manner along a top surface adjacent to a distal end thereof. The appendage 56 provides removable attachment of the blade compartments 58 via molded-in rectangular slot portions 57a being sized and positioned to provide a friction fit to corresponding integral tab portions 57b molded into a bottom surface of each blade compartment 58. Each blade compartment 58 further comprises a cylindrical magnet 59 being adhesively or otherwise mounted within the tab portion 57b which acts to attract the metallic portion of the blade 110, thereby positioning and securing the blade 110 during cleaning.

As the door 52 is closed against the front panel 22, the appendage 56 and loaded blades 110 enter the reservoir 38 through the top opening, are submerged into the solution 100, and subsequently acted upon by the solution 100 for a period of time until cleaned.

Figure 6A:
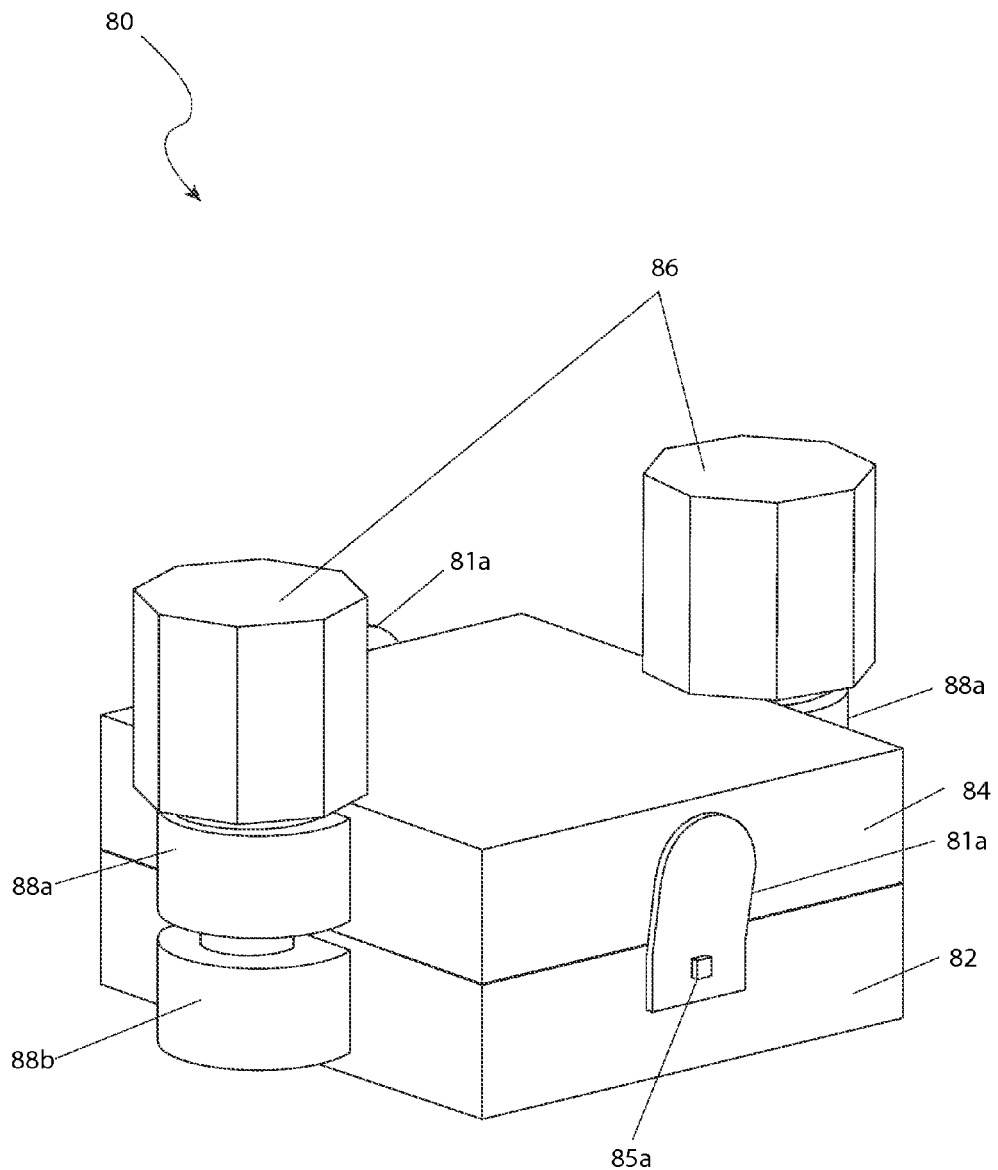
FIG. 6a is a perspective view of a travel cartridge portion 80 of the razor blade storage and sterilization device 10, according to a preferred embodiment of the present invention; and, FIG. 6b is an exploded view of the travel cartridge 80, according to a preferred embodiment of the present invention.
Figure 6B:
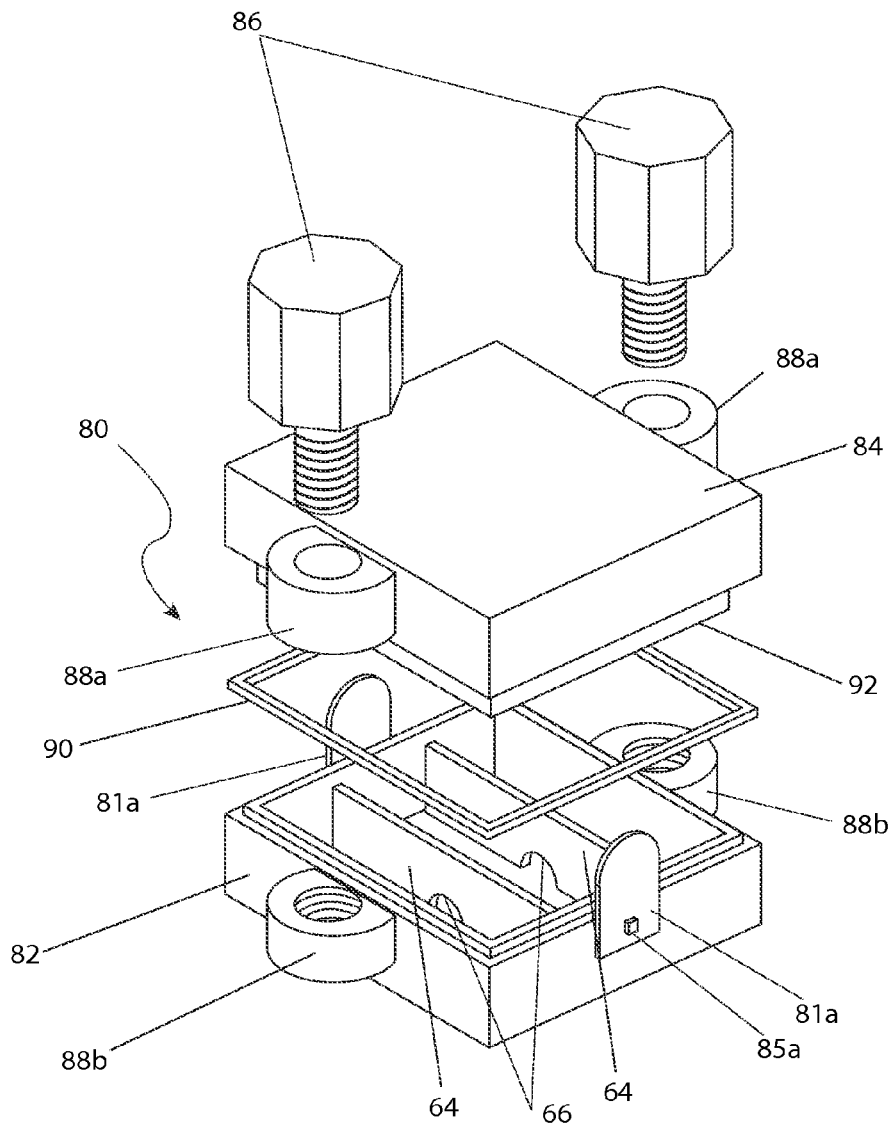

Referring now to FIGS. 6a and 6b, perspective and exploded views of a travel cartridge portion 80 of the device 10, according to a preferred embodiment of the present invention, are disclosed. The travel cartridge 80 provides a sealed enclosure to store and sterilize a plurality of blades 110 in a portable manner. The travel cartridge 80 my be positioned within the blade storage recess portion 32 in a similar manner as the blade rack 150, or removed for remote use such as while traveling (see FIGS. 1 and 3). The travel cartridge 80 allows insertion of up to three (3) blades 110 in a similar manner as the previously described blade rack 150.

The travel cartridge 80 allows a user to transport a plurality of cleaned and disinfected blades 110 while separated from the container 20. The travel cartridge 80 provides a protective and sealed rectangular enclosure further comprising lower enclosure half 82 and an upper enclosure half 84, being sealed together along a joining equator area via a rectangular gasket 90. The enclosure halves 82, 84 are secured to each other via installation of threaded knob fasteners 86 into integrally-molded fastener aperture portions 88a, 88b located along opposing outer surfaces of each enclosure half 82, 84. The knob fasteners 86 are envisioned to comprise threaded shafts with cylindrical knurled head portions, allowing finger-tightening by a user. The lower enclosure half 82 comprises two (2) equally-spaced lateral dividers 64 allowing insertion of up to three (3) blades 110 in a similar manner as the previously described blade rack 150. The dividers 64 further comprise integral semi-circular drain features 66 to allow removal of residual solution 100. In use, one (1) to three (3) blades 110 are inserted between the divider portions 64 and a volume of solvent 100 is poured into the lower enclosure half 82. The upper half 84 is then affixed by threadingly engaging the fasteners 86 into the fastener apertures 88a, 88b. The upper enclosure half 84 comprises a rectangular non-porous rubber pad portion 92 being adhesively affixed to an inner surface which acts to hold the included blades 110 in position. The travel cartridge 80 allows a user to maintain a quantity of blades 110 in a disinfected state over an extended period of time.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the device 10, it would be installed as indicated in FIG. 1.

The method of preparing the device 10 to clean blades 10 may be achieved by performing the following steps: acquiring the device 10; positioning the device 10 for use by resting the feet 29 upon a level surface; unscrewing the lid 40 from the reservoir aperture portion 36 of the container 20; grasping the reservoir handle 39; lifting and removing the reservoir 38 upwardly through the reservoir aperture portion 36; filling the reservoir 38 with solution 100 up to a desired level; replacing the reservoir 38 by nesting a reservoir floor portion 41 of the reservoir 38 into the reservoir recess portion 37 of the bottom panel portion 35a of the container 20; and, replacing the lid 40 onto the container 20. The device 10 is now ready for use.

The method of utilizing the device 10 for cleaning blades 110 may be achieved by performing the following steps: releasing the door 52 by rotating the latch handle 60; pivoting the door 52 outwardly to an open state to gain access to the appendage portion 56 of the blade cleaning assembly 50; installing at least one (1) blade compartment 58 onto the appendage 56 by inserting the tab portion 57b of the blade compartment 58 into the slot portion 57a of the appendage 56, if not previously installed; placing at least one (1) blade 110 into a respective blade compartment 58; closing the door 52 to submerge the blade compartments 58 and included blades 110 into the solution 100; securing the door 52 in a closed state by rotating the latch handle 60; and, allowing the blades 110 to soak in the solution 100 for a period of time.

The method of retrieving and utilizing the blades 110 for shaving may be achieved by performing the following steps: retrieving at least one (1) blade 110 by rotating the latch handle 60; pivoting the door 52 outwardly to lift the blades 110 out of the solution 100 and gain access to the clean blades 110; removing a blade 110 from a blade compartment 58; installing the clean and disinfected blade 110 onto a razor handle 105 in a conventional manner; utilizing the clean blade 110 in conjunction with a razor handle 105 to perform shaving in a normal manner; placing the assembled razor handle 105 and blade 110 into the razor storage compartment 96 until needed again; repeating the blade cleaning and disinfecting process as described above, to restore the blade 110 as needed; and, benefiting from a compact and effective means to clean and disinfect razor blades 110, thereby increasing a usable razor blade life afforded a user of the present invention 10.

The method of maintaining the device 10 may be achieved by performing the following steps: replacing waste solvent 100 periodically by removing the lid 40; removing the reservoir 38; dumping the soiled solution 100; adding a quantity of new solution 100; and, replacing the reservoir 38 and lid 40. Cleaning the device 10 periodically as needed by disassembling and individually washing the portions of the device 10.

The travel cartridge 80 may be utilized to transport or store blades 110 by performing the following steps: removing the travel cartridge 80 from the blade storage recess 32 by pinching the second clips 81b together and pulling the travel cartridge 80 from the container 20; placing the lower enclosure half portion 82 of the travel cartridge 80 upon a level surface; removing the fasteners 86 from the fastener apertures 88a, 88b; removing the upper enclosure half 84; placing at least one (1) blade 110 within the lower enclosure half 82; adding a volume of solvent 100 into the lower enclosure half 82 sufficient to cover the blades 110; replacing the upper enclosure half 84; securing the enclosure halves 82, 84 together by replacing the fasteners 86; inserting and retaining the travel cartridge 80 into the blade storage recess 32 using the second clips 81b for future use; or, retaining and transporting the travel cartridge 80 in a detached manner during such activities as traveling, camping, or the like; and, benefiting from the portability of cleaned and disinfected blades 110 while utilizing the travel cartridge 80.

The travel cartridge 80 and blade rack 150 allow a user to maximize a number of available clean and disinfected blades 110 by utilizing the blade cleaning assembly 50 to clean and disinfect a plurality of blades 110 as previously described.

The cleaned and disinfected blades 110 may be moved from the blade cleaning assembly 50 into the travel cartridge 80 and/or the blade rack 150 while an additional quantity of blades 110 may be cleaned and disinfected using the blade cleaning assembly 50.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A razor blade storage and sterilization system comprising:
   a container comprising an upper panel, a lower panel, a front panel, a rear panel, a first side panel, and a second side panel;
   a reservoir aperture disposed within said upper panel;
   a reservoir recess disposed within an inner side of said lower panel;
   a lid removably attached to a top of said container to removably cover said reservoir aperture;
   a blade cleaning aperture disposed within said front panel;
   a blade cleaning assembly hingedly attached to said front panel within subjacent to said blade cleaning aperture;
   a reservoir comprising a tray having an open top;
   a razor storage compartment disposed within said second side panel;
   a blade storage recess disposed within said first side panel; and,
   a blade storage means configured for storing and securing at least one razor blade therein, said blade storage means removably housed within said blade storage recess;
   wherein said reservoir is removably inserted into said container via said reservoir aperture;
   wherein said reservoir is adapted to receive a cleaning solution;
   wherein said blade cleaning assembly covers said blade cleaning aperture when closed;
   wherein said blade cleaning assembly is adapted to receive at least one razor blade; and,
   wherein said blade cleaning assembly is movable to position said at least one razor blade within said reservoir for submersion into said cleaning solution.

2. The system of claim 1, wherein said panels are joined at vertical corner portions by decorative and rounded integral corner features.

3. The system of claim 2, further comprising a foot portion integrated into a bottom of each of said corner feature.

4. The system of claim 1, wherein said razor storage compartment comprises an upper semi-circular compartment opening.

5. The system of claim 1, wherein said lid further comprises an integral cylinder portion which protrudes downwardly and engages said reservoir aperture.

6. The system of claim 5, wherein said lid further comprises a gripping recess on opposing sides.

7. The system of claim 1, wherein said blade cleaning assembly further comprises:
   a door hingedly attached to said front panel;
   a latch having a handle on an outer side of said door and a latch appendage on an inner side of said door; and,
   an arcuate appendage having at least one removably attached blade compartment and extending inward from an inner side of said door;
   wherein said door comprises a shape corresponding to said blade cleaning aperture; and,
   wherein said blade compartment is configured to receive and retain said at least one razor blade therewithin.

8. The system of claim 7, wherein said blade compartments are aligned along a central longitudinal axis of said appendage.

9. The system of claim 8, wherein said appendage further comprises at least one slot portion configured to receive a depending tab portion of each of said blade compartments.

10. The system of claim 9, wherein each blade compartment further comprises a magnet disposed within said tab portion;
    wherein said magnet provides a magnetic attraction to an individual razor blade when stored within the blade compartment.

11. The system of claim 1, wherein said reservoir further comprises:
    an open-top cylindrical vessel having a reservoir floor; and,
    an integral reservoir handle located along an upper rear surface of a first side thereof;
    wherein said reservoir comprises a diameter enabling removal and insertion through said reservoir aperture; and,
    wherein said reservoir nests within said reservoir recess.

12. The system of claim 11, wherein said reservoir floor further has a key feature disposed therewithin;
    wherein said key feature of said reservoir correspondingly mates with a receiver of said reservoir recess in order to position said second side of said reservoir towards said front panel.

13. The system of claim 1, wherein said blade storage recess comprises a rectangular recess having a pair of locking features on opposing sides thereof;
    wherein said blade storage means is removably attached to said pair or locking features.

14. The system of claim 13, wherein said blade storage means is a blade rack, comprising a five-sided rectangular enclosure having a pair of integral clip portions located along opposing outer surfaces thereof; and,
    at least one lateral divider within said enclosure to define adjacent blade storage compartments, each further having a drain feature;
    wherein each blade storage compartment is configured to receive and retain a razor blade; and,
    wherein said pair of clip portions correspondingly mate with said pair of locking features.

15. The system of claim 13, wherein said blade storage means is a travel cartridge comprising:
    a lower enclosure half having a proximal side and a pair of first fastener aperture features on opposing outer sidewalls thereof;
    an upper enclosure half having a proximal side and a pair of second fastener aperture features on opposing outer sidewalls thereof;
    a non-porous pad adhesively affixed to an inner surface of said upper enclosure half;

a rectangular gasket disposed between said proximal sides of said lower enclosure half and said upper enclosure half;

a pair of fasteners each removably attaching said lower enclosure half to said upper enclosure half via an aligned first aperture feature and second aperture feature pairs;

at least one lateral divider within said lower enclosure half to define adjacent blade storage compartments, each further having a drain feature; and, a pair of integral clip portions located along opposing outer sidewalls of said lower enclosure half;

wherein said travel cartridge comprises a shape corresponding to said blade storage recess;

wherein each blade storage compartment is configured to receive and retain a razor blade;

wherein said travel cartridge is adapted to receive a cleaning solution; and, wherein said pair of clip portions correspondingly mate with said pair of locking features.

* * * * *